United States Patent [19]

Bär et al.

[11] 4,340,542

[45] Jul. 20, 1982

[54] PROCESS AND EQUIPMENT FOR THE CONTINUOUS MANUFACTURE OF TRIOXAN

[75] Inventors: Helmüt Bär, Offenbach am Main; Herbert Mader, Nauheim; Karl-Friedrich Mück; Paül Zorner, both of Wiesbaden, all of Fed. Rep. of Germany

[73] Assignee: Hoechst Aktiengesellschaft, Frankfurt am Main, Fed. Rep. of Germany

[21] Appl. No.: 201,751

[22] Filed: Oct. 29, 1980

[30] Foreign Application Priority Data

Oct. 31, 1979 [DE] Fed. Rep. of Germany ....... 2943984

[51] Int. Cl.$^3$ .......................................... C07D 323/06
[52] U.S. Cl. ................................... 549/368; 549/347; 549/369; 549/430
[58] Field of Search ........................................ 260/340

[56] References Cited

U.S. PATENT DOCUMENTS

| | | | |
|---|---|---|---|
| 2,864,827 | 12/1958 | Baer et al. | 260/340 |
| 3,325,513 | 6/1967 | Bamford | 260/340 |
| 3,426,040 | 2/1969 | Langecker | 260/340 |
| 3,483,214 | 12/1969 | Sperber et al. | 260/340 |
| 3,732,252 | 5/1973 | Komazawa et al. | 260/340 |

FOREIGN PATENT DOCUMENTS 1543390 11/1972 Fed. Rep. of Germany .
1429161 1/1966 France .

*Primary Examiner*—Norma S. Milestone
*Attorney, Agent, or Firm*—Curtis, Morris & Safford

[57] ABSTRACT

The invention relates to a process for the continuous manufacture of trioxan, if appropriate together with cyclic formals, from aqueous formaldehyde solutions in a circulation reactor with an evaporator, wherein the vapor/liquid mixture, before it enters the reactor, is separated into the vapor phase and the liquid phase, and subsequently the two phases are fed separately to the reactor. In particular, high space-time yields can be achieved by the process according to the invention. Moreover, equipment for carrying out this process is a subject of the invention.

3 Claims, 1 Drawing Figure

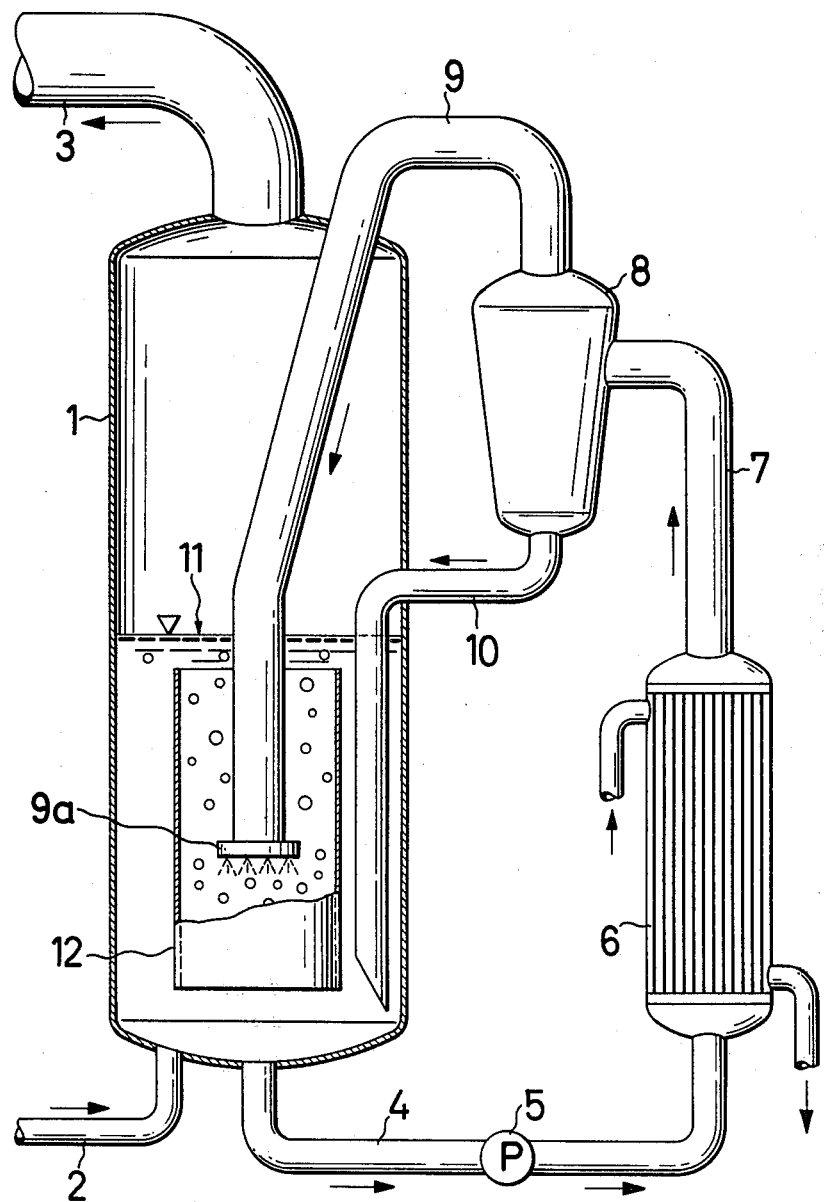

PROCESS AND EQUIPMENT FOR THE CONTINUOUS MANUFACTURE OF TRIOXAN

The manufacture of trioxan from aqueous formaldehyde solution is described at various places in the literature (compare Walker, Formaldehyde, Reinhold Publ. New York, 3rd edition, 1964, pages 198-199). The trioxan formed at elevated temperatures in the presence of acid catalysts is here separated off by distillation from the reaction mixture. The vapor from the synthesis, also containing by-products from the synthesis, in addition to trioxan, water and formaldehyde, is in most cases rectified, according to U.S. Pat. No. 2,304,080, in a rectifying column placed on top of the reactor, or it is rectified, according to British Pat. No. 1,012,372, in a column provided with a rectifying section and a stripping section. The trioxan-rich fraction obtained is worked up further by extraction and/or by another known separation process.

It is known that the time yields (g of trioxan per kg of formaldehyde and per hour) in the synthesis of trioxan are low. According to German Pat. No. 1,135,491, for example, time yields of 152 g of trioxan per kg of formaldehyde and per hour are obtained by a simple distillation of the reaction mixture from the reaction vessel. The low time yields have the consequence that long residence times are required in the manufacture of trioxan from aqueous formaldehyde solutions. Moreover, large reaction volumes are also necessary in order to obtain industrially satisfactory space-time yields (g of trioxan per 1 of reaction volume and time).

To increase the space-time yields in the synthesis of trioxan, it has already been proposed to displace the chemical equilibrium between formaldehyde, water and trioxan in the reaction mixture to the greatest possible extent by working at high rates of vaporization. This procedure, however, leads to low concentrations of trioxan in the vapor from the synthesis (compare E. Bartholome, Chem. Ing. Techn. 43 (1971), 597). Working-up of such reaction vapors is very energy-intensive because of the low concentration of trioxan.

Furthermore, German Auslegeschrift No. 1,543,390 has disclosed a process for which 1,090 g of trioxan per kg of formaldehyde and per hour are mentioned as the maximum value of the time yield. According to this process, aqueous formaldehyde solution is heated to the boil in the usual manner in the presence of acid catalysts in a circulation vaporizer, and the trioxan-rich vapors from the synthesis are then passed through a column placed on top of the reactor. Fully reacted reaction liquid which is in chemical equilibrium is passed through this column in counter-current relationship to the vapor from the synthesis. This has the result that the concentration of trioxan in the vapors from the synthesis, even at high rates of vaporization, reaches the thermodynamic equilibrium value which is obtained otherwise only with low rates of vaporization and with total mixing and which corresponds to the phase equilibrium of trioxan in the gaseous phase and in the liquid phase.

The disadvantage of the process according to German Auslegeschrift No. 1,543,390 is, however, that additional equipment items are required which represent a considerable increase in the actual reactor volume and hence a lowering of the space-time yields. Thus, in the process described, the process devices which come into contact with the reaction liquid consists of the actual reactor, an evaporator, a pump, a long pipe, if appropriate with a delay vessel, and a column with inserts. All these components must be manufactured from materials which are resistant to a hot acid formaldehyde solution which, for example, contains sulfuric acid, at a temperature of about 100°-110° C. The general disadvantages of corrosion-resistant reactors are described in German Auslegeschrift No. 2,103,687. If the space-time yields are then calculated, the resulting values are substantially lower than the time yields indicated in German Auslegeschrift No. 1,543,390.

German Auslegeschrift No. 2,428,719 describes a process for the separation of trioxan from aqueous solutions which contain trioxan together with formaldehyde, according to which 5 to 15% by weight of the solutions are distilled off at temperatures below 100° C. under reduced pressure and with residence times of less than 1 minute, and the trioxan is subsequently isolated from the distillate. The low time yields are a disadvantage of this procedure.

Finally, proposals have also already been made for achieving high space-time yields of trioxan even at high throughputs by means of an arrangement in which, in a forced circulation reactor, the vapor/liquid mixture leaving the evaporator is introduced below the liquid level of the fully reacted reaction mixture in the reactor in order to reach the phase equilibrium and the vapor stream from the synthesis leaves from the top of the reactor.

The present invention now relates to a process for the continuous manufacture of trioxan from aqueous formaldehyde solutions in the presence of acid catalysts in a forced circulation reactor with an evaporator, and with residence times between 2 and 240 minutes, the vapor/liquid mixture leaving the evaporator being introduced below the liquid level of the reaction mixture in the reactor and the vapor from the synthesis leaving the reactor, preferably from its top zone, which process comprises separating the vapor/liquid mixture, before it enters the reactor, into a vapor phase and a liquid phase and subsequently returning the two phases separately to the reactor.

A further subject of the invention is a continuous process for the simultaneous manufacture of trioxan and cyclic formals whereby an aqueous formaldehyde solution which contains at least one diol and/or at least one epoxide is treated in the above manner.

Finally, the invention also relates to the equipment as claimed in claims 4 to 7.

According to the process of the invention, concentrations of trioxan, which almost correspond to the equilibrium value, are obtained in the vapor from the synthesis, even at high rates of vaporization; at the same time, pulsation phenomena, such as are to be expected in the case of irregular vaporization and in the case of two-phase flow, are largely avoided.

The trimerization reaction of formaldehyde to give trioxan takes place in a manner known per se, by the reaction of aqueous formaldehyde solutions of 30-80% strength in general, preferably 40-70% strength, if appropriate with the addition of the known anti-foam agents, in the presence of the acid catalysts known for this purpose, such as mineral acids, strong organic acids or a quantity, of corresponding catalytic activity, of another acid catalyst. As the acid catalysts, which must be less volatile than the reaction mixture, sulfuric acid, phosphoric acid, p-toluenesulfonic acid or acid ion exchangers have proved useful. The quantity is not critical and amounts as a rule to 2 to 25%, preferably 2 to 10%.

If, by the variant according to the invention, a mixture of trioxan and at least one cyclic formal is to be manufactured, 1 to 25% by weight, preferably 2 to 15% by weight, relative to formaldehyde, of at least one diol and/or at least one epoxide are added to the aqueous formaldehyde solution.

The diols which can be used for this purpose are above all 1,2-diols, 1,3-diols and α,ω-diols. In place of the 1,2-diols, the corresponding epoxides, or mixtures of the two, can also be employed in the same way. Preferably, diols are used, the cyclic formals of which have boiling points of less than 150° C. and/or form low-boiling azeotropes (<150° C.) with water or are volatile with steam. For example, ethylene glycol, ethylene oxide, propylene 1,2-glycol, propylene oxide, propylene 1,3-glycol, butane-1,2-diol, butane-1,3-diol, butane-1,4-diol and but-3-ene-1,2-diol have proved suitable. Preferably, ethylene glycol or ethylene oxide, propylene 1,2-glycol and butane-1,4-diol are here employed according to the invention, and ethylene glycol or ethylene oxide are employed with particular preference.

The residence time of the reaction mixture in the reactor system is 2 to 240 minutes, preferably 5 to 120 minutes and with particular preference 15 to 60 minutes. The temperatures of the reaction mixture are between 50° C. and 150° C., preferably 95° C. and 110° C., depending on the pressure.

The reaction product consisting of trioxan, formaldehyde and water as well as, if appropriate, cyclic formals is vaporized in the circulation evaporator. This can be carried out under normal pressure, under reduced pressure, for example a pressure between 150 and 950 mbar, or under elevated pressure, for example a pressure of 1-4 bar. Preferably, the process is carried out under normal pressure or under a slightly elevated pressure.

In the process according to the invention, the degree of vaporization (quotient of the vaporized quantity of product and the quantity of product circulating through the vaporizer × 100) of the reaction mixture in the evaporator is, for example, between 0.1 and 25%, preferably between 1 and 20% and with particular advantage between 6 and 14%.

According to the process of the invention, the vapor/liquid mixture leaving the evaporator is separated into the liquid phase and the vapor phase by means of devices known for this purpose, such as precipitators, and is fed to the reactor vessel through separate pipes which preferably enter the vessel above the liquid level. At least the pipe for the vapor, which pipe enters the reactor preferably in the region near the top portion of the reactor, specifically in the vicinity of its highest point or directly at its highest point, is here designed as a dip pipe, that is to say the pipe extends downwards to a point below the liquid level. The dipping into the reaction mixture should here be arranged to be as deep as possible, in order to ensure optimum mass transfer and optimum mixing off and diffusing of gas in the reactor contents (principle of the air-lift pump). The dipping depth should, for example, be 20-80%, preferably 30-70%, of the reactor level used. The liquid level in the reactor vessel, the dipping depth, the suction line, the type of pump and the pump arrangement must here be matched in such a way that no cavitation can occur in the pump impeller, because the reaction liquid is in the state of boiling.

To improve the mass transfer between the reactor liquid and the gaseous phase coming from the evaporator, additional intimate mixing and diffusing of gas in the reactor contents can be effected by distributors (separator elements) known for this purpose, such as baffles arranged cylindrically around the dip pipe.

The liquid phase leaving the precipitator is preferably also introduced into the reactor liquid with a sufficient dipping depth below the liquid level, in order to prevent a breakthrough of the vaporous fraction through this return pipe.

The vapor mixture from the synthesis, leaving the reactor system, is passed in the conventional manner, either as vapor or as a condensate, to a rectification device, such as is described, for example, in British Pat. No. 1,012,372, and is thus enriched by distillation. The trioxan-rich fraction obtained which may also contain cyclic formals, can then be purified, for example by extraction with a water-immiscible solvent for trioxan and, if appropriate, for cyclic formals such as methylene chloride, and by subsequent neutralization and fractional distillation or crystallization. Other known separation processes can also be employed for this purpose, such as are described, for example, in Process Economics Program, Stanford Institute Report 23 (1967) page 181, or in German Offenlegungsschrift No. 1,570,335.

The process according to the invention is particularly advantageous in process engineering terms since, apart from, for example, a pump installed between the reactor and the evaporator, no increase in the reaction space due to additional units is necessary to ensure that, even at high rates of vaporization, the vapor generated in the synthesis has the highest possible trioxan content which corresponds to the equilibrium value in the gas phase for the distribution equilibrium of trioxan, water and formaldehyde in the liquid phase and the gaseous phase. According to previously described processes, this trioxan content can be achieved only when operating at low rates of vaporization or by the more expensive procedure described in German Auslegeschrift No. 1,543,390. According to the invention, space-time yields are thus achievable which are substantially higher than those obtained by the processes described previously.

In addition, the process according to the invention makes it possible to synthesize trioxan with a minimum specific energy requirement; thus, it has a favorable energy balance.

Moreover, the procedure according to the invention is distinguished by the fact that the formation of by-products such as formic acid, is repressed due to the short residence times when high rates of vaporization are used. Low concentrations of catalyst acid or the use of ion exchangers exhibit a similar effect.

The reaction is carried out in a known forced circulation reactor with an evaporator, a separating device (precipitator) for the vapor phase and liquid phase being arranged, according to the invention, downstream of the evaporator. Forced circulation vaporizers, consisting of a reaction kettle, pump and vaporizer, such as are described, for example, in Ullmann, Volume 1 (1951), 3rd edition, pages 533-537, are particularly suitable.

Preferably, the reactor for this is an upright cylindrical construction and has a flow-controlled feedline for the starting mixture and a line for taking off the distillate. The flow-controlled feedline is here located preferably at the lower end of the reactor, while the take-off line is preferably fitted at the top of the reactor.

The pipe which leads via a pump to the evaporator is preferably also located at the lower end of the reactor. The delivery rate of the pump is here not critical and can fluctuate within wide limits, for example between 30 and 300 m³/hour. The pipe leaving the evaporator then leads into the precipitating device, of conventional design, for the separation of the vapor phase and liquid phase. Two pipes which are to carry the vapor phase and liquid phase respectively then start from this precipitating device and enter the reactor, at least the vapor pipe being designed as a dip pipe with a gas-diffuser device. Preferably, distributors (separating elements), such as cylindrically arranged baffles, which favor an upward-circulating flow in the gas-diffusing zone and a backflow of the cooled liquid towards the vessel bottom, are located around this dip pipe.

The vapor pipe preferably enters the reactor in the region of the reactor top, in order to ensure that asymmetrical reaction forces which arise in the case of lateral entry and can lead to damage to the nozzle present at the entry point and to the surrounding inner wall of the reactor, are largely avoided. This is achieved most advantageously when this pipe ends at the highest point of the reactor top and, correspondingly, runs in the reactor in the direction of the longitudinal axis of the reactor.

The pipe which conveys the liquid phase and which as a rule leads laterally into the cylindrical part of the reactor, reaches preferably, according to the invention, down below the liquid level, that is to say it is likewise formed as a dip pipe. An adequate depth must here be chosen so that a breakthrough of the vaporous fraction through the return pipe is avoided. This is the case if the dipping depth is at least equal to that of the dip pipe for the vapor phase. In the first case, however, it is preferably at least 25% greater than in the case of the dip pipe for the vapor phase.

In the case where the pipe for the liquid phase is not designed as a dip pipe—and this is also possible according to the invention—it must be ensured by suitable measures that no breakthrough of vapor can take place. For example, this can be done in such a way that the liquid pipe leaving the precipitator, before entering the reactor, is formed as a U-pipe having a leg length of at least the dipping depth of the dip pipe for the vapor phase (siphon)

The scope of the invention also includes a variant, according to which the liquid pipe ends in the reactor below the surface of the liquid.

Appropriately, a manhole is provided in the upper part, for cleaning the reactor. Additionally, the reactor is advantageously insulated to prevent radiant heat loss. It can also contain means for regulating the temperature of the reactor wall, for example a double jacket, through which a temperature-regulating medium flows, and pipe coils or half-pipe coils, or electrical heating elements.

In addition, the reactor can also contain the conventional inserts and measuring instruments, for example for the temperature and level of the liquid. Liquid particles, which may have been carried over in the vapor from the synthesis, leaving the reactor, can be retained by a so-called demister of corrosion-resistant material, which is located at the start of the gas exit line.

The attached FIGURE shows an example of equipment according to the invention. The cylindrical, upright reactor vessel (1) has a flow-controlled feedline (2) and the gas exit line (3). A pump (5) is inserted in the pipe (4) connecting the reactor-vessel (1) with the evaporator (6) which, specifically, is a tube baffle exchanger in this case. The line (7) leaving the vaporizer ends in the precipitator (8) from which the vapor pipe (9) and the liquid pipe (10) start. These two are designed as dip pipes, that is to say they run down to a point below the liquid level (11). The dip pipe (9) has a gas-diffuser device (9a) at its end. It is concentrically surrounded by a cylindrical distributor (separator element) (12) for the purpose of improving the mass transfer between the liquid and gaseous phases.

The examples which follow will explain the invention in more detail.

EXAMPLES

The reaction was carried out in the equipment according to FIG. 1; the dipping depth of the vapor pipe was 70% of the reactor level.

1,000 g of a mixture consisting of 90 parts of a 63.5% strength aqueous formaldehyde solution and 10 parts of concentrated sulfuric acid were initially introduced into the reaction vessel in each case. The temperature of the vessel was adjusted to 95° C. The mixture was pumped by means of the pump through the evaporator, the latter being heated to different degrees, depending on the desired rate of vapor from the synthesis (trioxan throughput). The vapor from the synthesis, leaving the system, was totally condensed in a quench system, and the condensate was tested for trioxan and formaldehyde content. Further 63.5% strength formaldehyde solution was added under flow control, corresponding to the vaporized fraction. The duration of the experiment was 6 hours in each case.

The results are compiled in Table 1 and Table 2, together with the comparative experiments.

It is seen in Table 1 (Examples 1-3) that the concentrations of trioxan in the vapor from the synthesis are independent of the degree of vaporization in the evaporator.

TABLE 1

| Example No. | Trioxan in the distillate % | Degree of vaporization % | Conversion to trioxan % | Residence time hours |
|---|---|---|---|---|
| 1 | 22.4 | 5.4 | 35.3 | 0.8 |
| 2 | 21.3 | 1.16 | 33.5 | 0.94 |
| 3 | 21.6 | 4.35 | 34.0 | 0.92 |

It can be seen from Table 2 that, with identical residence times, the concentrations of trioxan in the vapor from the synthesis are greater than 20 percent by weight, both in the process according to the invention and in the comparative example (according to German Auslegeschrift No. 1,543,390).

The process according to the invention is distinguished, however, by substantially higher space-time yields, because the reaction volumes are significantly smaller than in the comparative process (German Auslegeschrift No. 1,543,390).

TABLE 2

| Example No. | Concentration of formaldehyde in the feed % | Residence time hours | Trioxan in the distillate % | Reactor volume | Ratio of the reaction volumes | Conversion to trioxan % | Ratio of the space-time yields |
|---|---|---|---|---|---|---|---|
| 4 | 63.5 | 0.3 | 22.0 | Reactor, vaporizer, pump | 1 | 34.6 | 1 |
| 5* | 63.5 | 0.3 | 20.8 | Reactor, pump, vaporizer, column, long pipe | 1.5-2 | 32.8 | 0.68-0.51 |

*according to Example 2 of German Auslegeschrift 1,543,390

We claim:

1. A process for the continuous manufacture of trioxan from aqueous formaldehyde solutions in the presence of an acid catalyst in a reactor system having a forced circulation reactor cooperating with an evaporator for vaporizing the reaction mixture from said reactor to form a mixture of vapor and liquid, said reaction mixture having a residence time in the reactor system in the range of 2 to 240 minutes, the mixture of vapor and liquid exiting the evaporator being fed in below the liquid level of the reaction mixture in said reactor, the vapor from the synthesis existing said reactor, which comprises separating the vapor and liquid mixture exiting said evaporator into respective vapor and liquid streams and separately feeding said respective vapor and liquid streams to the reactor.

2. The process of claim 1 wherein the mixture of vapor and liquid exiting the evaporator is fed to the reactor at a point 30% to 70% below the liquid level of the reaction mixture in said reactor.

3. The process of claim 1 or 2 wherein the rate of vapor exiting the reactor system is 6% to 14% relative to the rate of reaction mixture circulating through the evaporator.

* * * * *